(12) United States Patent
Isaacson et al.

(10) Patent No.: US 11,185,259 B2
(45) Date of Patent: Nov. 30, 2021

(54) SMART OBTURATOR WITH SENSOR AND SMART OBTURATOR ASSEMBLY

(71) Applicant: Becton, Dickinson and Company, Franklin Lakes, NJ (US)

(72) Inventors: S. Ray Isaacson, Layton, UT (US); Mark Hunter, Herriman, UT (US); Paul Walker, Sandy, UT (US); Jeff O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 365 days.

(21) Appl. No.: 15/697,112

(22) Filed: Sep. 6, 2017

(65) Prior Publication Data

US 2019/0069812 A1    Mar. 7, 2019

(51) Int. Cl.
*A61B 5/145*     (2006.01)
*A61M 25/00*    (2006.01)
*A61B 5/01*      (2006.01)
*A61B 5/00*      (2006.01)
*A61M 39/02*    (2006.01)

(52) U.S. Cl.
CPC .............. *A61B 5/145* (2013.01); *A61B 5/01* (2013.01); *A61B 5/14503* (2013.01);
(Continued)

(58) Field of Classification Search
CPC ....... A61B 5/01; A61B 5/145; A61B 5/14503; A61B 5/6852; A61M 2025/0002;
(Continued)

(56) References Cited

U.S. PATENT DOCUMENTS 5,308,318 A * 5/1994 Plassche, Jr. ..... A61M 25/0147
                                                                 604/540
2009/0275815 A1* 11/2009 Bickoff .............. A61B 5/14532
                                                                 600/345
(Continued)

FOREIGN PATENT DOCUMENTS

JP        H09173461        7/1997
JP        2003505131       2/2003
(Continued)

*Primary Examiner* — Joanne M Hoffman
*Assistant Examiner* — Alexei Bykhovski
(74) *Attorney, Agent, or Firm* — Kirton McConkie; Craig Metcalf; Kevin Stinger (57) ABSTRACT

An obturator assembly includes an obturator at least partially positionable within a lumen of a device. The obturator has a distal end with a tip portion and an opposing proximal end. A sensor assembly is at the tip portion. The sensor assembly is configured to sense one or more environmental characteristics and to generate one or more signals representative of the one or more environmental characteristics. A hub is operatively coupled to the obturator. The hub is also operatively coupled to electronic circuitry that is coupled in signal communication with the sensor assembly. In certain embodiments, the electronic circuitry is configured to receive the one or more signals from the sensor assembly and transmit the one or more signals to remote reception circuitry and/or display a datum representative of the one or more environmental characteristics on a display of the hub.

17 Claims, 4 Drawing Sheets

(52) U.S. Cl.
CPC .......... *A61B 5/6852* (2013.01); *A61M 25/00* (2013.01); *A61M 25/0069* (2013.01); *A61M 2025/0002* (2013.01); *A61M 2025/0018* (2013.01); *A61M 2025/0019* (2013.01); *A61M 2025/0079* (2013.01); *A61M 2039/0267* (2013.01)

(58) Field of Classification Search
CPC .. A61M 2025/0018; A61M 2025/0019; A61M 2025/0079; A61M 2039/0267; A61M 25/00; A61M 25/0069
See application file for complete search history.

(56) References Cited

U.S. PATENT DOCUMENTS

| | | | |
|---|---|---|---|
| 2015/0157216 A1* | 6/2015 | Stigall | A61B 5/0215 600/486 |
| 2016/0278856 A1* | 9/2016 | Panescu | A61B 5/150954 |
| 2017/0049378 A1* | 2/2017 | Schipper | A61B 5/6852 |
| 2017/0143348 A1* | 5/2017 | Cressman | A61B 17/12186 |
| 2017/0245885 A1* | 8/2017 | Lenker | A61B 17/3478 |

FOREIGN PATENT DOCUMENTS

| | | | | |
|---|---|---|---|---|
| JP | 2012509104 | | 4/2012 | |
| JP | 2012532726 | | 12/2012 | |
| JP | 2015519959 | | 7/2015 | |
| WO | 2011/005814 | | 1/2011 | |
| WO | WO 2011005814 | * | 1/2011 | ............... A61N 1/00 |

* cited by examiner

SMART OBTURATOR WITH SENSOR AND SMART OBTURATOR ASSEMBLY

TECHNICAL FIELD

The present application relates generally to an obturator assembly. More specifically, the present application relates to a smart obturator assembly including a sensor assembly at a distal end of an obturator to sense environmental characteristics including, for example, different markers, proteins, and/or chemicals in the patient's blood stream.

BACKGROUND

Conventional obturators are utilized to prevent an IV catheter from becoming occluded with clotting blood. If the IV catheter remains open after use, blood can reflux back into the catheter tip and begin to coagulate, obstructing a flow of blood through the tip portion of the IV catheter and preventing continued use of the IV catheter for subsequent therapy. When this happens, the IV catheter must be removed and a replacement IV catheter set to gain vascular access. Bio-films and fibrin can also form over the tip portion of the IV catheter and obstruct blood flow into the IV catheter. In an attempt to prevent this obstruction, some conventional obturators are formed of a solid plastic piece that is inserted from a proximal end of the IV catheter to close or seal the opening of the lumen at the distal end of the IV catheter. The conventional obturator includes an adapter, such as a Luer connector lock, that fits on the proximal end to create a fluid-tight seal, while the distal tip portion of the obturator is positioned in the distal end of the IV catheter to prevent the IV catheter from becoming occluded. Introducing the conventional obturator through the proximal end of the catheter may increase a risk of patient infection.

BRIEF SUMMARY OF SOME EXAMPLE EMBODIMENTS

In a first aspect, a smart obturator assembly suitable for use with a device, such as a catheter having a distal end and an opposing proximal end. The catheter includes a cannula at the distal end and extending toward the proximal end of the catheter. A connector is at the proximal end of the catheter. The catheter forms a lumen extending between the distal end and the proximal end. An obturator is positionable within the lumen. The obturator includes a distal end having a tip portion at least partially positionable within the lumen and a proximal end opposite the distal end. A sensor assembly is at the tip portion. The sensor assembly is configured to sense one or more environmental characteristics within a patient's blood vessel and to generate one or more signals representative of the one or more environmental characteristics. Electronic circuitry is coupled in signal communication with the sensor assembly. The electronic circuitry is configured to receive the one or more signals and transmit the one or more signals to a remote reception circuitry and/or display a datum representative of the one or more environmental characteristics on a display of the smart obturator assembly. In a particular embodiment, the electronic circuitry is located within or operatively coupled to a hub. The hub is operatively coupled to the obturator and configured to provide a pass through connection from the sensor assembly to the electronic circuitry and/or the hub may display a datum representative of the one or more environmental characteristics on a display in the hub.

In another aspect, an obturator includes a distal end having a tip portion and a proximal end opposing the distal end. A sensor assembly at the tip portion is configured to sense one or more environmental characteristics, generate one or more signals representative of the one or more environmental characteristics, and transmit the one or more signals to electronic circuitry coupled in signal communication with the sensor assembly. The electronic circuitry is configured to receive the one or more signals and process the one or more signals and/or transmit the one or more signals to a remote reception circuitry.

In yet another aspect, an obturator assembly includes an obturator having a distal end with a tip portion at least partially positionable within a lumen of a device, such as a catheter, and an opposing proximal end. A sensor assembly at the tip portion is configured to sense one or more environmental characteristics and to generate one or more signals representative of the one or more environmental characteristics. A hub is operatively coupled to the obturator. The hub includes electronic circuitry coupled in signal communication with the sensor assembly. The electronic circuitry is configured to receive the one or more signals and transmit the one or more signals to a remote reception circuitry and/or display a datum representative of the one or more environmental characteristics on a display in the hub.

DETAILED DESCRIPTION

Various embodiments are described below with reference to the drawings in which like elements generally are referred to by like numerals. The relationship and functioning of the various elements of the embodiments may better be understood by reference to the following detailed description.

However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE, ISO standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments as shown in FIGS. 1-10, an obturator for use with an example obturator assembly includes a distal end having a tip portion and an opposing proximal end. A sensor assembly at the tip portion is configured to sense one or more environmental characteristics, generate one or more signals representative of the one or more environmental characteristics, and transmit the one or more signals to electronic circuitry, e.g., positioned in or operatively coupled to a hub, of the obturator assembly. For example, in certain embodiments, the hub includes electronic circuitry coupled in signal communication with the sensor assembly. In alternative embodiments, the electronic circuitry may be an independent component of the obturator assembly, a component remote from the obturator assembly, or the electronic circuitry may be positioned in or operatively coupled to a component of the obturator assembly other than the hub. The electronic circuitry is configured to receive the one or more signals and transmit the one or more signals to a remote reception circuitry and/or display a datum representative of the one or more environmental characteristics, as described herein, on a display in the hub.

In certain example embodiments, an obturator includes a distal end having a tip portion and a proximal end opposing the distal end. A sensor assembly is positioned at the tip portion. The sensor assembly is configured to sense one or more environmental characteristics, generate one or more signals representative of the one or more environmental characteristics, and transmit the one or more signals to a hub coupled in signal communication with the sensor assembly. The hub is configured to receive the one or more signals and transmit or pass-through the one or more signals to remote reception circuitry, for example. Additionally or alternatively, a datum representative of the one or more environmental characteristics may be displayed on a display of the hub.

In certain example embodiments, an obturator assembly includes an obturator having a distal end having a tip portion at least partially positionable within a lumen of a device, such as a catheter. The catheter has a distal end and an opposing proximal end and an adapter at the proximal end. The catheter forms the lumen extending between the distal end and the opposing proximal end. A sensor assembly at the tip portion is configured to sense one or more environmental characteristics and to generate one or more signals representative of the one or more environmental characteristics. A hub is operatively coupled to the obturator. The hub includes electronic circuitry coupled in signal communication with the sensor assembly. The electronic circuitry is configured to receive the one or more signals and transmit the one or more signals to remote reception circuitry. Additionally or alternatively, a datum representative of the one or more environmental characteristics may be displayed on a display of the hub.

As described herein, an example smart obturator assembly includes a sensor assembly having a sensor or an array of sensors at the distal end of the obturator, e.g., at or near the tip portion of the distal end of the obturator and/or at or near the distal end of the catheter. In certain example embodiments, each sensor is positioned within a vein or an artery to directly contact the patient's blood stream. Each sensor is operatively coupled to electronic circuitry coupled to or integrated into the hub of the obturator assembly, for example, using lead wires that are molded into or are attached to an outside surface or an inside surface of the obturator, for example. The hub at the proximal end of the obturator assembly is configured with one or more of a variety of electronic and/or communication components to provide power, data transmission, data collection, and data analysis capabilities, as well as other capabilities.

Each sensor may be configured to sense one or more environmental characteristics including, without limitation, different markers, proteins, and/or chemicals in the patient's blood stream. Alternatively, the sensor assembly may include an array of sensor, with each sensor configured to sense one or more environmental characteristics. The sensor assembly may be integrally formed with the obturator or the sensor assembly may be modularized. In certain example embodiments, the obturator provides a socket or a recessed area for housing the sensor assembly. One or more conductive pads are positioned within or near the recessed area for electrical communication with the sensor assembly. For example, two conductive pads electrically couple, e.g., provide signal communication between, the sensor assembly and a thermocouple operatively coupled to the hub or the electronic circuitry on or in the hub to sense a temperature. In alternative example embodiments, a wire configuration including a plurality of lead wires may be operatively coupled to the electronic circuitry to provide suitable communication protocols, e.g., USB level communication, which can enable a wide range of sensors, data rates and/or data types on a well-defined BUS. Other suitable communication protocols include, for example, simple plugin, Wi-Fi, BLUETOOTH® wireless technology, a universal serial bus connector, Radio Frequency Identification (RFID), Near Field Communication (NCF, a derivative of RFID), and self-contained displays. The distal end of the obturator and/or the sensor assembly may be flush with the distal end of catheter, proud of the distal end of the catheter (i.e., extend past the distal end of the catheter) or recessed into the distal end of the catheter (i.e., proximal to the distal end of the catheter) depending on a desired configuration for a particular sensor or sensor array. The sensor assembly may also provide access through a catheter for in-vivo monitoring as desired.

In certain example embodiments, the obturator assembly has a customizable interface between the obturator and the catheter. This customization may be accomplished with features on the catheter adapter (e.g., a small-bore connector, such as a small-bore connector having a 6% tapered fluid connection per International Standard ISO 80369 for liquids and gases in healthcare applications) that must be present in order for the sensor assembly to work properly or with added features. In certain embodiments, a bump, projection, or suitable feature may be present when operatively coupling the obturator to the catheter to sense the bump, projection, or feature and allow the obturator assembly to work properly. As such the obturator assembly can fit properly with catheters having slightly different catheter diameters, lengths, and/or relevant dimensions. Thus, the embodiments described herein may be configured to work properly with various catheters to ensure that the obturator assembly safely and effectively occludes the lumen opening at the distal end of the catheter, as well as provides sensing capabilities.

Referring now to the figures, and initially to FIGS. 1-4, an example smart obturator assembly 10 includes a hub 12 having a distal end 14 and an opposing proximal end 16. As used herein, the terms "distal" and "distally" refer to a location, a position, and/or a direction situated away from hub 12, i.e., a point of origin or attachment, while the terms "proximal" and "proximally" refer to a location, a position and/or a direction situated toward hub 12, i.e., the point of origin or attachment.

A catheter 20 is operatively coupled to hub 12. In example embodiments, catheter 20 includes a cannula 22 extending from a distal end 24 toward an opposing proximal end 26 of catheter 20. At proximal end 26, catheter 20 includes an adapter or a body, such as a small-bore connector 28 shown in FIGS. 1 and 2, for example, to couple proximal end 26 of catheter 20 to distal end 14 of hub 18. In certain embodiments, small-bore connector 28 is a connector having a 6% tapered fluid connection per ISO 80369 for liquids and gases in healthcare applications. Hub 12 is coupled to proximal end 26 of catheter 20 with a fluid-tight connection. In example embodiments, catheter 20 forms or defines a lumen 30 extending between distal end 24 and proximal end 26 of catheter 20 at hub 12.

Figure 3:
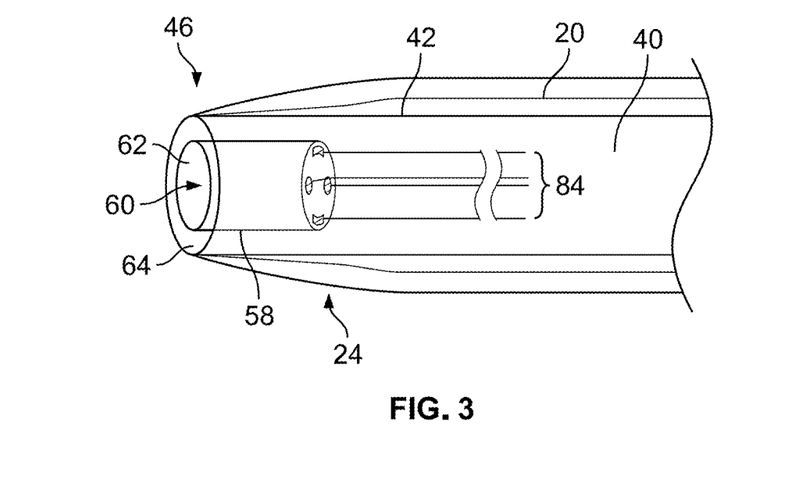
FIG. 3 is a partial perspective side view of the example obturator assembly shown in FIG. 2.
Figure 4:
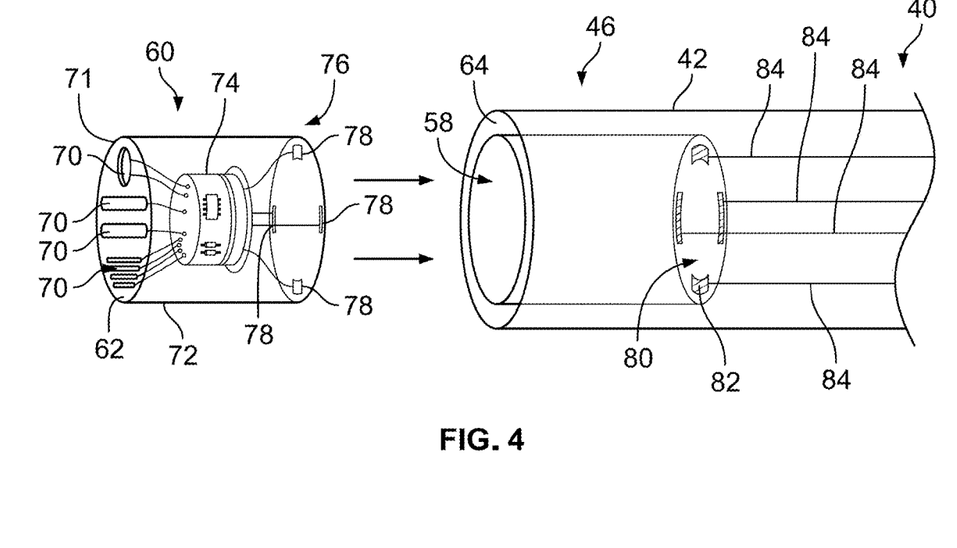
FIG. 4 is an exploded, partial perspective side view of the example obturator shown in FIG. 2.
Figure 5:
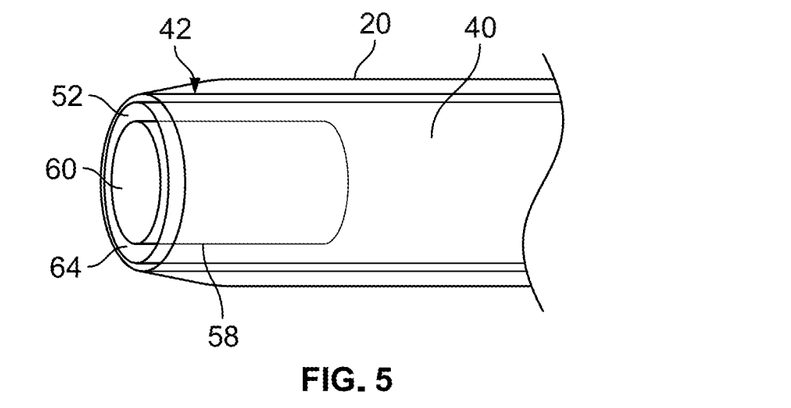
FIG. 5 is a partial perspective side view of an example obturator assembly including a distal end of the obturator flush with a distal end of the catheter according to example embodiments.
Figure 6:
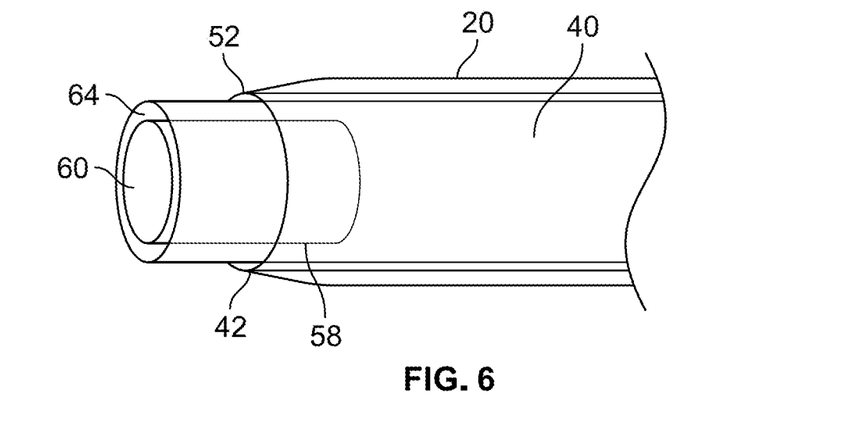
FIG. 6 is a partial perspective side view of an example obturator assembly including a distal end of the obturator proud of a distal end of the catheter according to example embodiments.
Figure 7:
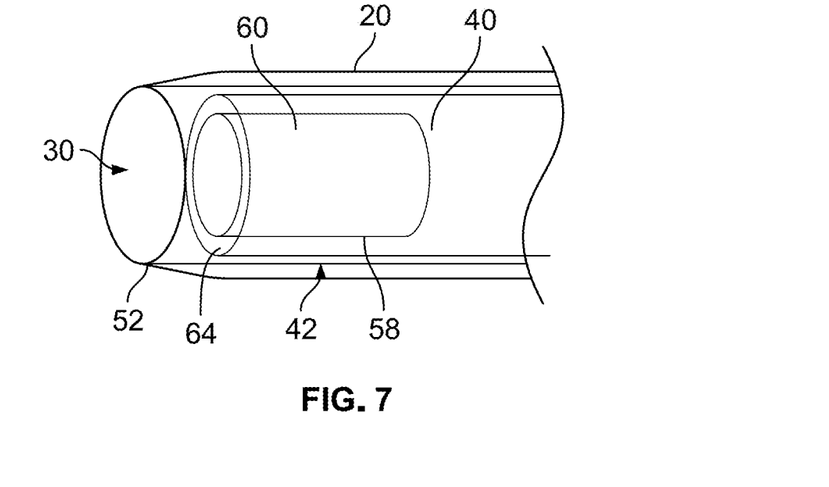
FIG. 7 is a partial perspective side view of an example obturator assembly including a distal end of the obturator recessed in a distal end of the catheter according to example embodiments.

Referring further to FIGS. 1-4, smart obturator assembly 10 includes an obturator 40 at least partially positioned within lumen 30. Obturator 40 has a distal end 42 and an opposing proximal end 44. In certain embodiments, obturator 40 includes a tip portion 46 at distal end 42. In certain example embodiments, tip portion 46 is at least partially positioned within lumen 30. Tip portion 46 transitions into a body 48 in a midsection of obturator 40 and body 48 transitions into a base 50 at proximal end 44 of obturator 40. In example embodiments, distal end 42 and, in certain embodiments, tip portion 46, prevents or limits fluid flow into lumen 30. Referring further to FIGS. 5-7, in particular embodiments, obturator 40 is flush with a terminal surface 52 of catheter 20 at distal end 24, as shown in FIG. 5, extends proud of terminal surface 52 of catheter 20 at distal end 24, as shown in FIG. 6, or is recessed in lumen 30, as shown in FIG. 7. In particular embodiments, obturator 40 is made of a suitable translucent material to act as a conduit for light-based disinfectant technology used in reducing bioburden in the intraluminal space, for example.

Figure 9:
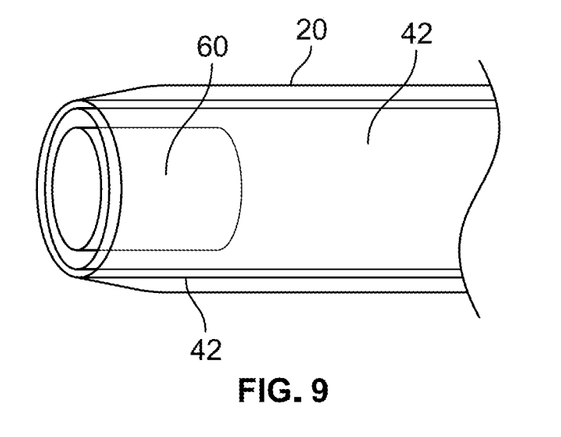
FIG. 9 is a partial perspective side view of an example obturator assembly with a distal end of the obturator flush with a distal end of the catheter according to example embodiments.
Figure 10:
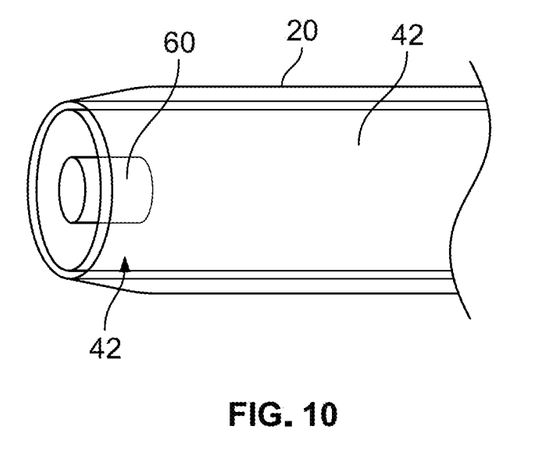
FIG. 10 is a partial perspective side view of an example obturator assembly with a distal end of the obturator flush with a distal end of the catheter according to example embodiments.

As shown, for example, in FIGS. 3-7, obturator 40 forms a recessed area 58 at distal end 42 of obturator 40. A sensor assembly 60 is positioned at or near distal end 42, e.g., on distal end 42 and/or at least partially within recessed area 58 at tip portion 46. In example embodiments, such as shown in FIGS. 5-7, sensor assembly 60 is positioned within recessed area 58 such that an end surface 62 of sensor assembly 60 is flush with an end surface 64 of obturator 40 at distal end 42. In alternative example embodiments, sensor assembly 60 may be only partially positioned within recessed area 58 such that end surface 62 extends outwardly from end surface 64 of obturator 40 at distal end 42. Referring further to FIGS. 9 and 10, in certain example embodiments, sensor assembly 60 has a constant diameter along a length of sensor assembly 60. An outer diameter of obturator 40 at distal end 42 may vary to properly fit in a lumen of differently-sized catheters, e.g., 14, 16, 18, 20, and 22 gauge catheters. In particular embodiments, the size, i.e., a diameter and/or a length, of sensor assembly 60 is minimized to fit in smaller-sized catheters. Sensor assembly 60 may be coupled to distal end 42 by press-fitting, molding, gluing, snapping, or pinning sensor assembly 60 to distal end 42, for example. Other coupling means known to those skilled it the art may be used to couple sensor assembly 60 to distal end 42.

Figure 8:
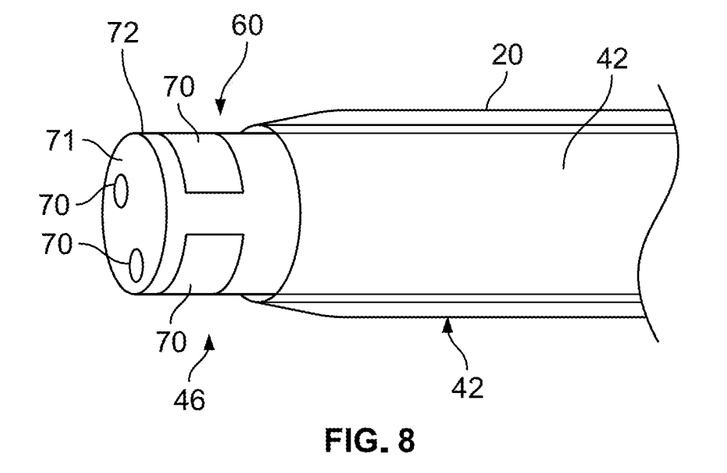
FIG. 8 is a partial perspective side view of an example obturator including a sensor assembly proud of a distal end of the catheter according to example embodiments.

Sensor assembly 60 is configured to sense one or more environmental characteristics within or related to a patient's blood or blood stream and generate and transmit one or more signals representative of the one or more environmental characteristics. For example, in example embodiments, sensor assembly 60 includes one or more sensors 70, e.g., one sensor 70 or a plurality of sensors 70. Referring further to FIGS. 4 and 8, for example, each sensor 70 is positioned at or on an end surface 71 of sensor assembly 70, as shown in FIGS. 4 and 8, and/or positioned on a perimeter surface 72 of sensor assembly 60, as shown in FIG. 8. In example embodiments, each sensor 70 of sensor assembly 60 is configured to measure one or more environmental characteristics including, without limitation, a temperature within a body lumen, a blood glucose level, a sodium level, a potassium level, a drug concentration level, a white blood cell count, a blood pressure within the body lumen, or any combination thereof. Further, sensor assembly 60 may include one or more particular sensors 70 including, without limitation, a temperature sensor, a sensor that senses a chemical within a patient's blood, a sensor that senses a marker in the patient's blood, a sensor that senses a protein in the patient's blood, or any combination thereof.

Figure 1:
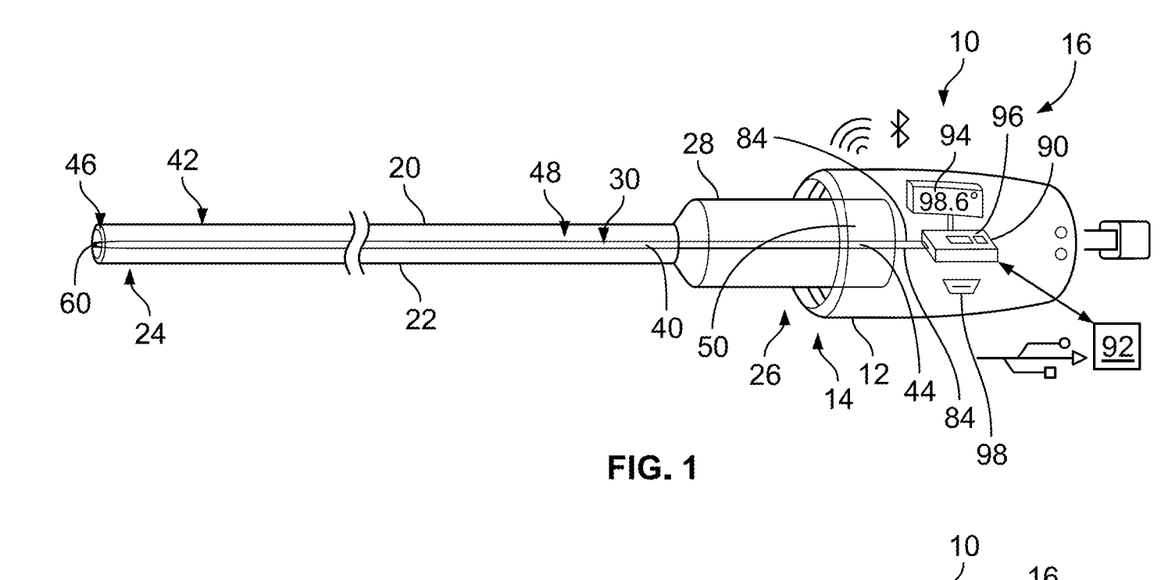
FIG. 1 is a perspective side view of an example obturator assembly according to example embodiments.

In example embodiments, sensor assembly 60 includes a plurality of sensors 70, as shown in FIGS. 4 and 8. Each sensor 70 is electrically coupled to, e.g., coupled in signal communication with, an electronic circuit 74 of sensor assembly 60. Electronic circuit 74 may include, for example, an integrated chip or an electronic circuit board. A first electrical contact interface 76 including one or more first electrical contacts 78, e.g., a plurality of spring contacts, is electrically coupled to, e.g., coupled in signal communication with, electronic circuit 74. With sensor assembly 60 positioned within recessed area 58, first electrical contact interface 76 is electrically coupled to a second electrical contact interface 80 positioned on and/or in distal end 42 of obturator 40 to electrically coupled second electrical contact interface 80 with sensor assembly 60. Second electrical contact interface 80 includes a plurality of second electrical contacts 82, e.g., a plurality of contact pads. Each second electrical contact 82 of the plurality of second electrical contacts 82 is electrically coupled to a respective first electrical contact 78 of the plurality of first electrical contacts 78. Referring further to FIGS. 1, 3, and 4, one or more electrical lead wires 84, e.g., a plurality of lead wires 84, extend through obturator 40 to electrically couple, e.g., couple in signal communication, sensor assembly 60 via second electrical contact interface 80 with electronic circuitry 90 operatively coupled to hub 12. In example embodiments, electric circuitry 90 is positioned on and/or within hub 12. In certain example embodiments, each electrical lead wire 84 is molded onto tip portion 46 or molded into tip portion 46. Electrical lead wire 84 may extend along a surface of a wall of obturator 40 or may be embedded or molded within at least a portion of a length of the obturator wall between distal end 42 and proximal end 26.

Figure 2:
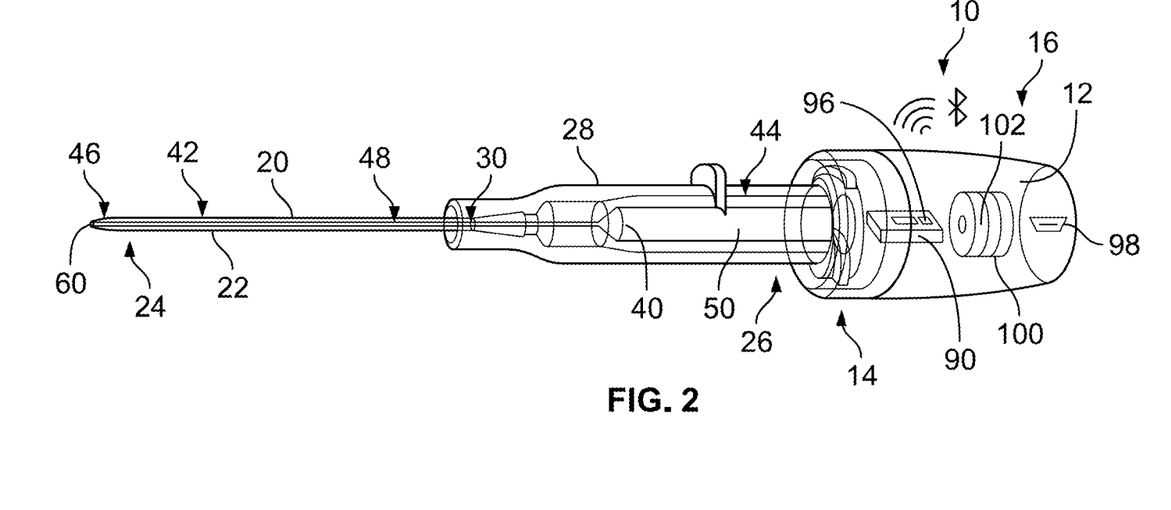
FIG. 2 is a perspective side view of an alternative example obturator assembly according to example embodiments.

Referring further to FIGS. 1 and 2, electronic circuitry 90 is configured to transmit signals to and receive signals from sensor assembly 60. Electronic circuitry 90 is also configured to transmit signals to and receive signals from remote reception circuitry 92 including an external processor operatively coupled to electronic circuitry 90. Additionally or alternatively, electronic circuitry 90 is configured to display a datum representative of the one or more environmental characteristics on a display 94 on or in hub 12. In certain embodiments, communication circuitry 96 is electrically coupled to, e.g., coupled in signal communication with, electronic circuitry 90 for wireless communication with remote reception circuitry 92 or an external processor. In certain embodiments, communication circuitry 96 and/or electronic circuitry 90 are located in or operatively coupled to hub 12. In these embodiments, communication circuitry 96 includes one or more circuits, such as a radio frequency identification circuit, a near field communication circuit, a BLUETOOTH® wireless technology circuit, a universal serial bus connector, one or more transmitters, or any suitable combination thereof. In particular embodiments, a connection port 98, e.g., a USB port, on and/or in hub 12 is configured for connecting electronic circuitry 90 with remote reception circuitry 92 or an external processor. In example embodiments, communication circuitry 96 provides active or passive near field communication that can be queried by an RFID or Near Field Reader, which provides power to and queries electronic circuitry 90, to which communication circuitry 96 may respond in a passive manner (with power supplied by the reader) or in an active manner (with additional power supplied inside hub 12, or powered by a connecting device, for example). Hub 12 may also include a compartment 100 housing a power source 102, e.g., a battery pack, as shown in FIG. 2 electrically coupled to electronic circuitry 90 to provide power to electronic circuitry 90 and/or sensor assembly 60. Power supply 102 may be integral to hub 12 or externally coupled to hub 12.

Hub 12, e.g., electronic circuitry 90, may include one or more processors and one or more computer-readable media, one or more communication interfaces, and one or more power sources. The communication interfaces may support both wired and wireless connection to various networks, such as cellular networks, radio, Wi-Fi networks, short range networks (e.g., BLUETOOTH® technology), and infrared (IR) networks, for example.

Depending on the configuration of electronic circuitry 90, the computer-readable media (and other computer-readable media described throughout) is an example of computer storage media and may include volatile and nonvolatile memory. Thus, the computer-readable media may include, without limitation, RAM, ROM, EEPROM, flash memory, and/or other memory technology, and/or any other suitable medium that may be used to store computer-readable instructions, programs, applications, media items, and/or data which may be accessed by electronic circuitry 90. The computer-readable media may be used to store any number of functional components that are executable on a processor. Electronic circuitry 90 may have additional features or functionality. For example, electronic circuitry 90 may also include additional data storage devices (removable and/or non-removable). The additional data storage media, which may reside in a control board, may include volatile and nonvolatile, removable and non-removable media implemented in any method or technology for storage of information, such as computer readable instructions, data structures, program modules, or other data. In addition, some or all of the functionality described as residing within electronic circuitry 90 may reside remotely from electronic circuitry 90, e.g., in remote reception circuitry 92, in some implementations. In these implementations, electronic circuitry 90 may utilize communication interfaces to communicate with remote reception circuitry 92 and utilize this functionality. Referring to FIGS. 1-10, in example embodiments, obturator 40 including sensor assembly 60 may be used independently of the other components of obturator assembly 10 and/or catheter 22 or may be used with any suitable combination of one or more components of obturator assembly 10 and/or catheter 22.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A smart obturator assembly, comprising:
an obturator positionable within a lumen of a catheter, the obturator comprising:
a distal end having a tip portion at least partially positionable within the lumen, wherein the tip portion comprises a recessed area, wherein a proximal end surface of the recessed area is formed by a wall of the obturator that comprises a plurality of electrical contacts configured to selectively couple to a sensor assembly, wherein the recessed area extends from a distal end surface of the obturator forming a distal opening to the proximal end surface such that the sensor assembly is configured to be inserted proximally into the recessed area; and
a proximal end opposite the distal end;
the sensor assembly at the tip portion, wherein the sensor assembly is disposed within the recessed area and contacts the proximal end surface of the recessed area formed by the wall of the obturator, wherein a proximal end surface of the sensor assembly comprises a plurality of other electrical contacts aligned with the plurality of electrical contacts, the sensor assembly configured to sense one or more environmental characteristics within a patient's blood vessel and to generate one or more signals representative of the one or more environmental characteristics;

electronic circuitry operatively coupled in signal communication with the sensor assembly, the electronic circuitry configured to receive the one or more signals and to at least one of transmit the one or more signals to remote reception circuitry or display a datum representative of the one or more environmental characteristics on a display of the smart obturator assembly, wherein the electronic circuitry comprises a plurality of lead wires extending from the plurality of contacts of the proximal end surface.

2. The smart obturator assembly of claim 1, further comprising a hub operatively coupled to the obturator, wherein the electronic circuitry is located in the hub.

3. The smart obturator assembly of claim 1, further comprising communication circuitry coupled in signal communication with the electronic circuitry for wireless communication with the remote reception circuitry.

4. The smart obturator assembly of claim 3, wherein the communication circuitry comprises a wired or wireless connection to a network.

5. The smart obturator assembly of claim 1, further comprising a connection port for connecting the electronic circuitry with the remote reception circuitry.

6. The smart obturator assembly of claim 1, further comprising a power source electrically coupled to the electronic circuitry to provide power to at least one of the electronic circuitry or the sensor assembly.

7. The smart obturator assembly of claim 6, wherein the power source is one of integral to a hub coupled to the obturator or externally coupled to the hub.

8. The smart obturator assembly of claim 1, wherein the device comprises a catheter forming the lumen and having a distal end, wherein the sensor assembly is flush with the distal end of the catheter, proud of the distal end of the catheter or recessed in the lumen.

9. The smart obturator assembly of claim 1, wherein the sensor assembly comprises a sensor positioned on a distal end surface of the sensor assembly.

10. The smart obturator assembly of claim 1, wherein the sensor assembly comprises one or more sensors configured to measure at least one of the following environmental characteristics: a temperature within a body lumen, a blood glucose level, a sodium level, a potassium level, a drug concentration level, a white blood cell count, a blood pressure within the body lumen, or a combination thereof.

11. The smart obturator assembly of claim 1, wherein the sensor assembly comprises one or more of the following sensors: a temperature sensor, a sensor that senses a chemical within a patient's blood, a sensor that senses a marker in the patient's blood, a sensor that senses a protein in the patient's blood, or a combination thereof.

12. The smart obturator assembly of claim 1, wherein an inner surface forming the recessed area is cylindrical between the distal end surface and the proximal end surface, wherein the inner surface abuts the proximal end surface.

13. The smart obturator assembly of claim 1, wherein a distal end surface of the sensor assembly is flush with a distal end surface of the obturator at the distal end.

14. The smart obturator assembly of claim 12, wherein the proximal end surface is generally transverse to a longitudinal axis of the obturator.

15. An obturator positionable within a lumen of a catheter, the obturator comprising:

a distal end having a tip portion at least partially positionable within the lumen, wherein the tip portion comprises a recessed area, wherein a proximal end surface of the recessed area is formed by a wall of the obturator that comprises a plurality of electrical contacts configured to selectively couple to a sensor assembly, wherein the recessed area extends from a distal end surface of the obturator forming a distal opening to the proximal end surface such that a sensor assembly is configured to be inserted proximally into the recessed area;

a proximal end opposing the distal end;

a sensor assembly at the tip portion, wherein the sensor assembly is disposed within the recessed area and contacts the proximal end surface of the recessed area, wherein a proximal end surface of the sensor assembly comprises a plurality of other electrical contacts aligned with the electrical contacts, the sensor assembly configured to sense one or more environmental characteristics, generate one or more signals representative of the one or more environmental characteristics, and transmit the one or more signals to electronic circuitry coupled in signal communication with the sensor assembly, the electronic circuitry configured to receive the one or more signals and transmit the one or more signals to remote reception circuitry.

16. The obturator of claim 15, further comprising a hub at the proximal end, the hub including a power source electrically coupled to the electronic circuitry to provide power to the electronic circuitry.

17. The obturator of claim 15, wherein an inner surface forming the recessed area is cylindrical between the outer end surface and the proximal end surface, wherein the inner surface abuts the proximal end surface, wherein the proximal end surface is generally transverse to a longitudinal axis of the obturator.

* * * * *